United States Patent [19]

Kreidl et al.

[11] Patent Number: 4,831,194
[45] Date of Patent: May 16, 1989

[54] PROCESS FOR THE PREPARATION OF NITRODIARYL SULFOXIDES

[75] Inventors: Janos Kreidl; Peter Turcsanyi; Zsuzsanna Aracs nee Trischler; Bela Stefko; Judit Meszaros nee Brill; Ida Deutsch nee Juhasz; Jeno Szilbereky; Eva Csizer; Szilard Vezer; Erik Bogsch, all of Budapest; Jozsef Bakos, Veszprem; Laszlo Szotyori, Veszprem; Balint Heil, Veszprem, all of Hungary

[73] Assignee: Richter Gedeon Vegyeszeti Gyar Rt., Budapest, Hungary

[21] Appl. No.: 76,675

[22] Filed: Jul. 23, 1987

Related U.S. Application Data

[60] Division of Ser. No. 833,834, Feb. 26, 1986, Pat. No. 4,710,323, which is a continuation-in-part of Ser. No. 706,704, Feb. 28, 1985, and a continuation-in-part of Ser. No. 706,705, Feb. 28, 1985, and a continuation-in-part of Ser. No. 706,707, Feb. 28, 1985.

[30] Foreign Application Priority Data

Feb. 29, 1984 [HU] Hungary ................. 813/84
Feb. 29, 1984 [HU] Hungary ................. 814/84
Feb. 29, 1984 [HU] Hungary ................. 815/84

[51] Int. Cl.$^4$ .................................. C07C 147/14
[52] U.S. Cl. .................................. 568/36; 260/513.7; 260/543 R; 514/646; 514/708; 564/430
[58] Field of Search .................. 568/36, 37, 27; 260/543 R, 513.7

[56] References Cited

U.S. PATENT DOCUMENTS

| | | | |
|---|---|---|---|
| 3,506,767 | 4/1970 | Frick et al. ........................ | 564/430 |
| 3,518,236 | 6/1970 | Hunter .............................. | 260/513.7 |
| 4,331,817 | 5/1982 | Throckmorton ................. | 564/430 |
| 4,457,875 | 7/1984 | Fournier et al. ................ | 260/543 R |

OTHER PUBLICATIONS

Kemer Chem. Ind. Res., Derwent Abstract of U.S.S.R. 857,123, Aug. 23, 1981.

*Primary Examiner*—Mary E. Ceperley
*Attorney, Agent, or Firm*—Herbert Dubno; Jonathan Myers

[57] ABSTRACT

The invention relates to a new process for the preparation of aminodiaryl sulfoxide derivatives of the formula (I),

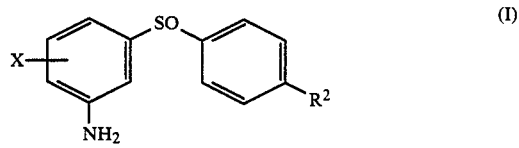

wherein X is halogen, alkoxy having from 1 to 6 carbon atoms or a group —(N,R,R$^1$), in which p1 R and R$^1$ are hydrogen or alkyl having from 1 to 6 carbon atoms, R$^2$ is hydrogen, halogen, alkyl having from 1 to 6 carbon atoms, alkoxy having from 1 to 6 carbon atoms or phenyl or phenylthio both optionally substituted by one or more identical or different halogen(s) and/or amino group(s), and acid addition salts thereof.

The compounds of formula (I) are pharmaceutically active, in particular are potent anthelmintics, or can be used as active ingredients in pesticidal compositions. The invention therefore relates to pharmaceutical and pesticidal compositions containing compounds of formula (I) or salts thereof as active ingredient.

Compounds of formula (I), in which the substituents are as defined above, but if X stands for a group —N(R,R$^1$) in which R and R$^1$ both represent hydrogen, and X is in para-position related to the sulfoxide group, then R$^2$ is other than hydrogen, halogen, alkyl having from 1 to 6 carbon atoms and alkoxy having from 1 to 6 carbon atoms, and the acid addition salts thereof, are new. These new compounds are also subject of the present invention.

8 Claims, No Drawings

PROCESS FOR THE PREPARATION OF NITRODIARYL SULFOXIDES

CROSS-REFERENCE TO RELATED APPLICATIONS

This application is a division of Ser. No. 833,834 filed Feb. 26, 1986, now U.S. Pat. No. 4,710,323, which is a continuation-in-part of Ser. Nos. 706,704; 706,705 and 706,707 all filed Feb. 28, 1985.

The invention relates to new nitrodiaryl sulfoxide derivatives, to a process for their preparation and pharmaceutical and pesticidal compositions containing them as active ingredient. More particularly, the invention concerns new nitrodiaryl sulfoxide derivatives of the formula (I)

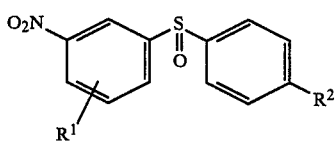
(I)

wherein
$R^1$ is halogen or alkoxy having from 1 to 6 carbon atoms,
$R^2$ is hydrogen, halogen, alkyl having from 1 to 6 carbon atoms, alkoxy having from 1 to 6 carbon atoms, or phenyl or phenylthio optionally substituted by one or more identical or different halogen(s) and/or nitro group(s).

According to another aspect of the invention there is provided a process for the preparation of the new compounds of the formula (I), wherein $R^1$ and $R^2$ have the same meanings as defined above, by reducing an arylsulfonyl halide of the formula (II)

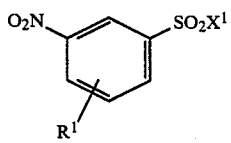
(II)

wherein
$R^1$ is as defined above, and
$X^1$ is halogen,
with an alkali metal sulfite, treating the arylsulfinate of the formula (III)

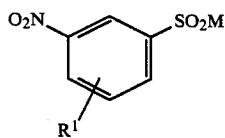
(III)

obtained, in which
$R^1$ is as defined above, and
M is an alkali metal,
with an acid, reacting the arylsulfinic acid of the formula (IV)

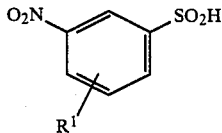
(IV)

obtained, in which $R^1$ is as defined above, or the arylsulfinate of formula (III), in which $R^1$ and M are as defined above, with a halogenating agent, and reacting the new arylsulfinyl halide of the formula (V)

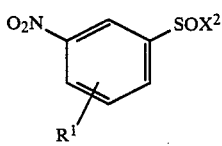
(V)

obtained, in which $R^1$ is as defined above and $X^2$ is halogen, with a benzene derivative of the formula (VI),

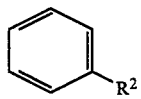
(VI)

wherein $R^2$ is as defined in connection with the formula (I), in the presence of a metal halide catalyst of the Lewis acid type.

The new compounds of the formula (I) are pharmaceutically active, and can in particular be used in the veterinary therapy, e.g. as nematocides, taenicides, etc., and preferably as anthelmintics, and show pesticidal, e.g. acaricidal, fungicidal, antimicrobial and herbicidal, preferably insecticidal activity.

The compounds of the formula (I) are further valuable intermediates in the preparation of other new and known, biologically active aromatic sulfoxide derivatives, such as benzimidazole and substituted diamino sulfoxide derivatives having anthelmintic and fungicidal activity, e.g. Oxfendazole. They can be prepared from the compounds according to the invention by reaction with an amine derivative, subsequent reduction and coupling with a carbamic acid derivative.

Compounds of the formula (I) are new. In the hitherto known nitro-substituted diaryl sulfoxides the nitro group was attached to one of the phenyl rings in the ortho- or para-position related to the sulfoxide group, and the other substituents were different from those in the compounds according to the invention as to their quality, number and position related to the sulfoxide group; while the only known compound containing an o-nitro group was unsubstituted. The structurally related, known diaryl sulfoxides were generally prepared by a different procedure, i.e. oxidation of the corresponding diaryl sulfides [Ber. 41, 2836 (1908), J. Am. Chem. Soc. 1381 (1948)].

In the formula (I) $R^1$ and $R^2$ as halogen represent fluorine, chlorine, bromine or iodine, preferably chlorine; while as alkoxy having from 1 to 6 carbon atoms they stand for any straight-chained or branched alkoxy group, e.g. methoxy, ethoxy, n-propoxy, isopropoxy, n-butoxy, sec.-butoxy, isobutoxy, n-pentoxy, isopentoxy, n-hexyloxy, isohexyloxy, etc., preferably methoxy. In the definition of $R^2$ the term "alkyl having from 1 to 6 carbon atoms" is used to refer to straight-chained or branched alkyl groups, e.g. methyl, ethyl, n-propyl, isopropyl, n-butyl, sec.-butyl, isobutyl, tert.-butyl, n-pentyl, isopentyl, n-hexyl, isohexyl, etc.

In the compounds of formula (III) M as an alkali metal preferably stands for potassium or sodium.

In the compounds of formulae (II) and (V) $X^1$ and $X^2$ as halogen represent fluorine, chlorine, bromine or iodine, preferably chlorine.

The intermediates of the formula (V) are new compounds, and their preparation is also within the scope of the present invention.

The reduction of the arylsulfonyl halides of the formula (II) with alkali metal sulfites is preferably carried out in an aqueous medium, by using the alkali metal sulfite in a slight excess, preferably in an amount of 1.1 to 4 moles related to 1 mole of arylsulfonyl halide. The reduction is performed at a temperature of 20° to 35° C., preferably 22° to 28° C. The reduction is preferably accomplished under mildly alkaline conditions, between pH 7 and 9, preferably 7.5 and 8.5, for example by adding to the reaction mixture an alkali metal bicarbonate, alkali metal carbonate or alkali metal hydroxide simultaneously. Alternatively, the above agents may be added to the reaction mixture prior to the addition of the reducing agent. The alkali metal components of the above reactants are preferably identical with the alkali metal of the alkali metal sulfite used as a reducing agent. The above alkaline agents serve also for acid binding. The alkali metal bicarbonates, carbonates or hydroxides can be used either in a solid form or in the form of their saturated aqueous solutions or simultaneously in both forms.

The acid treatment of the compounds of the formula (III) is preferably carried out with a strong mineral acid, preferably concentrated aqueous hydrochloric acid, sulfuric acid, etc. The mineral acid is preferably used in an excess amount. The arylsulfinic acid obtained after hydrolysis is very pure (has a purity of at least 98%) and stable, contrary to the arylsulfinic acids prepared earlier by different processes. Compounds of formula (IV) are obtained in a very high yield, which considerably exceeds the yield of the hitherto known processes [Houben-Weyl, 9, 307].

Both the arylsulfinates of formula (III) and the arylsulfinic acids of formula (IV) can be reacted with a halogenating agent, to yield the corresponding arylsulfinyl halide of the formula (V). As a halogenating agent an inorganic or organic halogenating agent can be used. Inorganic halogenating agents include for example the compounds of sulfur and phosphorus with halogen or with halogen and oxygen. Typical representatives of these compounds are thionyl chloride, phosphorus trichloride, phosgene, phosphorus pentachloride, phosphorus oxychloride, and a combination of phosphorus oxychloride and chlorine. Organic halogenating agents include organic acid halides, such as oxalyl chloride. The arylsulfinyl halides of the formula (V) are new compounds, which are considerably more stable then the differently substituted arylsulfinyl halides known in the art.

During the reaction of the compounds of formula (V) with the compounds of formula (VI) as a metal halide catalyst of the Lewis acid type any catalyst conventionally used in Friedel-Crafts acylations, e.g. preferably aluminium trichloride, can be used. According to a preferred embodiment of the reaction compounds of the formula (V) are reacted with the compounds of the formula (VI) without isolation, directly after elimination of the halogenating agent. The metal halide catalyst of the Lewis acid type is preferably used in an amount of 1.1 to 1.8 moles relates to 1 mole of the arylsulfinyl halide of formula (V). The reaction is performed between 0° C. and 80° C., preferably 25° C. and 42° C.

The process according to the invention yields the new nitrodiaryl sulfoxides in a high purity (at least 98%) with excellent yield (90 to 96% related to the corresponding arylsulfinic acid, and about 85% related to the corresponding arylsulfonyl halide). The process according to the invention can easily be carried out even on an industrial scale.

The reaction mixtures can be processed by conventional techniques, for example extraction, filtration, evaporation, precipitation with water, elimination of the solvent or the excess of reactants, decantation, etc.

The compounds of the formula (I) can be subjected, if desired, to further purification, e.g. recrystallization. The solvents used for recrystallization are selected depending on the solubility and crystallization properties of the compound to be crystallized.

The active compounds of the formula (I) may be formulated for therapeutic purposes. The invention therefore relates also to pharmaceutical compositions comprising as active ingredient at least one compound of formula (I), in association with pharmaceutical carriers and/or excipients. Carriers conventional for this purpose and suitable for parenteral or enteral administration as well as other additives may be used. As carriers solid or liquid compounds, for example water, gelatine, lactose, starch, pectin, magnesium stearate, stearic acid, talc, vegetable oils, such as peanut oil, olive oil, etc. can be used. The compounds can be formulated as conventional pharmaceutical formulations, for example in a solid (globular and angular pills, dragées, e.g. hard gelatine capsules) or liquid (injectable oily or aqueous solutions or suspensions) form. The quantity of the solid carrier can be varied within wide ranges, but preferably it is between 25 mg. and 1 g. The compositions optionally contain also conventional pharmaceutical additives, such as preserving agents, wetting agents, salts for adjusting the osmotic pressure, buffers, flavoring and odoring substances.

The compositions according to the invention optionally contain the compounds of formula (I) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

For use as pesticides, the compounds of the formula (I) are formulated as conventional formulations, e.g. solutions, emulsions, soluble powders, suspensions, powder compositions, aerosol compositions, suspension and emulsion concentrates, powders for seed dressing. The compounds can be used for impregnating natural and synthetic materials, may be formulated as microcapsules, using polymeric substances and materials suitable for coating seeds, or can be converted into formulations supplied with burnable filling, such as smoke patrons, boxes, spirals, and warm or cold fog compositions, which may be applied by ULV (ultra-low-volume) technique.

The pesticidal compositions can be prepared in a manner known per se, for example by admixing the active ingredients with carriers, i.e. liquid solvents, liquified gases under pressure and/or solid carriers. If desired, also surfactants, emulsifying and/or dispersing and/or foaming agents can be added to the system. If water is used as a carrier, as a co-solvent organic solvents may also be employed. The liquid solvents essentially include aromatic compounds such as xylene, toluene or alkylnaphthalenes; chlorinated aromatic or chlorinated aliphatic hydrocarbons such as chlorobenzene, chloroethylene or methylene chloride; aliphatic hydrocarbons, such as cyclohexane or paraffines such as mineral oil fractions, as well as alcohols such as butanol or glycol and the ethers and esters thereof; ketones such as acetone, methyl ethyl ketone, methyl isobutyl ketone or cyclohexanone; strongly polar solvents such as dimethyl formamide, dimethyl sulfoxide and water. As liquefied gaseous carriers for example aerosol propellants such as halogenated hydrocarbons, butane, propane, nitrogen and carbon dioxide are meant. As solid carriers for example natural fossil meals, e.g. kaoline, clay earth, talc, chalkstone, quartz, attapulgite, montmorillonite or diatomaceous earth, and synthetic fossil meals such as highly dispersed silicic acid, alumina and silicates are employed. As carriers for granulates for example broken and fractionated natural rocks, e.g. calcite, marbel, pumice, sepiolite, dolomite, and granulates of inorganic and organic meals, as well as granulates prepared from organic materials such as sawdust, coconut, shell, corn husk and tobacco stems can be used. As emulsifying agents and/or foaming agents non-ionic and anionic emulsifiers such as polyoxyethylene fatty acid ethers, polyoxyethylene fatty alcohol ethers, e.g. alkylarylpolyglycol ether, alkylsulfonates, alkylsulfates, arylsulfonates and protein hydrolysates, while as dispersing agents e.g. lignine, sulfite waste liquors and methyl cellulose may be employed.

The pesticidal compositions according to the invention may contain also adhesives such as carboxymethyl cellulose, natural and synthetic, powdery, granular or latex-like polymers, e.g. acacia gum, polyvinyl alcohol, polyvinyl acetate, etc.

The pesticidal compositions according to the invention may further contain various pigments such as inorganic pigments, e.g. iron oxide, titanium dioxide, ferrocyane blue and organic pigmetns, e.g. alizarine, azometal phthalocyanine pigments, as well as micronutrients, e.g. iron, manganese, boron, copper, cobalt, molybdenum and zinc salts.

The pesticidal compositions generally contain 0.1 to 95% by weight, preferably 0.5 to 90% by weight of active ingredient.

The active ingredients may be applied in the form of commercial formulations and/or ready-to-use formulations prepared therefrom.

The active ingredient concentration of the ready-to-use formulations prepared from the commercial pesticidal compositions may vary within wide limits, and generally is between 0.000 000 1 and 95% by weight, preferably 0.01 and 10% by weight.

The route of application always depends on the specific formulation used.

The invention also relates to a new process for the preparation of nitraminodiaryl sulfoxide derivatives. More particularly, the invention concerns a new process for preparing the partially new nitraminodiaryl sulfoxide derivatives of formula (VII):

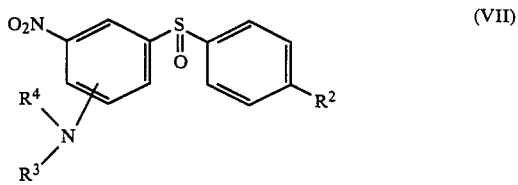

wherein
$R^3$ and $R^4$ represent hydrogen or alkyl having from 1 to 6 carbon atoms.

According to the invention the nitraminodiaryl sulfoxide derivatives of formula (VII), are prepared by reacting a nitrodiaryl sulfoxide derivative of the formula (I),

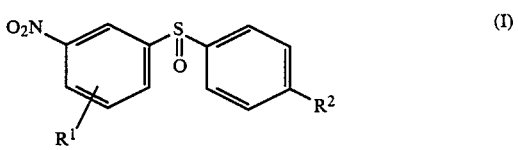

with an amine derivative of the formula (VIII),

wherein
$R^3$ and $R^4$ are as defined above, and
A is hydrogen or a group —CO—$R^5$, in which
$R^5$ is hydrogen, alkyl having from 1 to 6 carbon atoms or a group —N($R^3$,$R^4$), in which
$R^3$ and $R^4$ are as defined above,
or a salt thereof.

In the definition of $R^2$, $R^3$, $R^4$ and $R^5$ the term "alkyl having from 1 to 6 carbon atoms" is used to refer to straight-chained or branched alkyl groups, such as e.g. methyl, ethyl, n-propyl, isopropyl, n-butyl, isobutyl, sec.-butyl, tert.-butyl, n-pentyl, isopentyl, n-hexyl and isohexyl groups.

The compounds of formula (VII) are pharmaceutically active, which can particularly be useful in the veterinary therapy as anthelmintics; and they show pesticidal, particularly acaridical, fungicidal and herbicidal properties.

The compounds of formula (VII) are further valuable intermediates in the preparation of other new and known bioactive aromatic sulfoxide derivatives, such as benzimidazole and substituted diamino sulfoxides having anthelmintic and fungicidal activity, e.g. Oxfendazol [5-(6)-phenylsulfinyl-2-carbomethoxyaminobenzimidazole]. These can be prepared from the compounds according to the invention by reduction and coupling with a carbamic acid ester derivative.

Compounds of formula (VII), in which the group —N($R^3R^4$) is in para-position with respect to the sulfoxide group, $R^2$ is hydrogen, $R^3$ and $R^4$ are identical and stand for hydrogen or methyl are known, while the other compounds of formula (VII) are new.

Of the compounds of formula (VII), those in which $R^2$, $R^3$ and $R^4$ each stands for hydrogen are disclosed in the German Patent Specifications Nos. 2,462,258 and 2,549,417, and are prepared by nitrating the corresponding 4-aminodiaryl sulfoxide. To avoid the oxidative sidereactions, in this process the amino groups should be protected by acylation and after the nitration the acylamino-nitro-diaryl sulfoxide obtained has to be desacylated. Therefore, the process, which would normally include only a nitration step, includes two additional reaction steps, i.e. becomes a three-step procedure. A further disadvantage of this process is that it yields a mixture of isomeric nitro-compounds, and the nitration is carried out with a mixture of foaming nitric acid and a small amount of concentrated sulfuric acid in an acetic acid medium containing acetic anhydride, which is highly explosive due to the formation of acetyl nitrate, especially when performed on industrial scale.

Compounds of formula (VII), in which $R^2$ is hydrogen and $R^3$ and $R^4$ are methyl are prepared according to Ann. Chim. (Rome), 60(7), 527-536 [Ref.: C.A. 74 (11), 53202B] by treating the corresponding diphenyl sulfides with nitric acid in nitromethane. Due to the use of the highly aggressive and dangerous nitric acid, in this process a substantial amount of by-product is formed as a result of the splitting of the bond between the sulfur atom and phenyl group; consequently the yield is reduced and the product obtained will be contaminated.

We have surprisingly found that by using as a starting material instead of 4-aminodiaryl sulfoxides, halogen- or alkoxy-substituted nitrodiaryl sulfoxides of the formula (I), the desired compounds can be obtained with an excellent yield, in a high purity, since both the halogen and the alkoxy group in a compound of formula (I) can efficiently be replaced by a suitable amine group. The reaction involves a very simple, single reaction step, proceeds without undesired side-reactions and can be carried out even on industrial scale without special safety measures.

In the process according to the invention as a compound of formula (VIII) for example ammonia, preferably as an aqueous solution, an aliphatic primary amine, such as methylamine, ethylamine, n-propylamine, isopropylamine, n-butylamine, sec.-butylamine, tert.-butylamine, etc., an aliphatic secondary amine, such as dimethylamine, diethylamine, diisopropylamine, dibutylamine, etc., an aliphatic monocarboxylic acid amide, e.g. formic acid amide, acetic acid amide, propionic acid amide, dimethyl formamide, or carbonic acid amides, such as urea, ammonium salts, such as ammonium chloride, ammonium carbonate, etc. are used.

The process according to the invention is carried out in an organic solvent, for example a mono- or polyfuncional aliphatic alcohol having from 1 to 8 carbon atoms, such as ethylene glycol, glycerine, diethylene glycol, their water-miscible monoalkyl esters, e.g. cellosolve, or other cyclic ethers, e.g. dioxane or tetrahydrofurane, etc. or in a mixture of any of these solvents with water. The reaction is preferably performed in a (1:4)-(4:1) mixture of an aliphatic alcohol and water. The reaction temperature is generally between 70° C. and 200° C., preferably 80° C. and 120° C., i.e. the reaction proceeds under very mild conditions, therefore practically is devoid of side reactions. This is very important since during amination reactions one generally has to count on side-reactions, such as the splitting off of sulfinic acid in the instant case, or the hydrolytic substitution of the halogen atom or alkoxy group. These theoretically possible reactions do, however, not take place in the process according to the invention. The process is preferably carried out using 2.0 to 50, preferably 2.5 to 20 moles of the compound of formula (VIII) or a salt thereof, related to one mole of a compound of formula (I).

The reaction mixture according to the invention is treated in a conventional manner. The product is generally obtained with a high yield, in a pure crystalline form.

The compounds of the formula (VII), if desired, can be subjected to further purification, e.g. recrystallization. The solvents used for recrystallization are selected depending on the solubility and crystallization properties of the compound to be crystallized.

As mentioned before, compounds of the formula (VII),

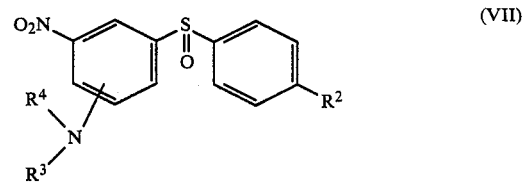

in which
$R^3$ and $R^4$ are hydrogen or alkyl having from 1 to 6 carbon atoms, and
$R^2$ is hydrogen, halogen, alkyl having from 1 to 6 carbon atoms, alkoxy having from 1 to 6 carbon atoms, or phenyl or phenylthio optionally substituted by one or more identical or different halogen(s) and/or nitro group(s),
with the proviso that if $R^2$ is hydrogen and the substituent —N($R^3$, $R^4$) is in para-position related to the sulfoxide group, $R^3$ and $R^4$ are other than hydrogen or methyl, are new. The invention relates also to these compounds.

According to a still further aspect of the invention there are provided pharmaceutical compositions comprising as active ingredient at least one compound of formula (VII), in which $R^3$, $R^4$ and $R^2$ are as defined above, without the proviso, in association with pharmaceutical carriers and/or excipients.

The invention further relates to pesticidal compositions comprising as active ingredient at least one compound of formula (VII), wherein $R^3$, $R^4$ and $R^2$ are as hereinbefore defined, without the proviso, in association with conventional carriers and optionally further additives.

The preferred pharmaceutical and pesticidal compositions include the new compounds of formula (VII), as hereinbefore defined.

The compounds of formula (VII) may be formulated for therapeutic purposes. Carriers conventional for this purpose and suitable for parenteral or enteral administration as well as other additives may be used. As carriers solid or liquid compounds, for example water, gelatine, lactose, starch, pectin, magnesium stearate, stearic acid, talc, vegetable oils, such as peanut oil, olive oil, arabic gum, polyalkylene glycols, and vaseline (registered Trade Mark), can be used. The compounds can be formulated as conventional pharmaceutical formulations, for example in a solid (globular and angular pills) or liquid (injectable oily or aqueous solutions or suspensions) form. The quantity of the solid carrier can be varied within wide limits, but preferably is between 25 mg. and 1 g. The compositions optionally contain also conventional pharmaceutical additives, such as preserving agents, wetting agents, salts for adjusting the osmotic pressure, buffers, flavoring and aroma substances.

The compositions according to the invention optionally contain the compounds of formula (VII) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

For use as pesticides, the compounds of the formula (VII) are formulated as conventional formulations, e.g. solutions, emulsions, soluble powders, suspensions, powder compositions, aerosol compositions, suspension and emulsion concentrates, powders for seed dressing. The compounds can be used for impregnating natural and synthetic materials, may be formulated as microcapsules, using polymeric substances and materials suitable for coating seeds, or can be converted into formulations supplied with a burnable filling, such as smoke patrons, boxes, spirals, and warm or cold fog compositions, which may be applied by ULV (ultra-low-volume) technique.

The pesticidal compositions can be prepared in a manner known per se, for example by admixing the active ingredients with carriers, i.e. liquid solvents, liquefied gases under pressure and/or solid carriers. If desired, also surfactants, emulsifying and/or dispersing and/or foaming agents can be added to the system. If water is used as a carrier, as a co-solvent organic solvents may also be employed. The liquid solvents essentially include aromatic compounds such as xylene, toluene or alkylnaphthalenes; chlorinated aromatic or chlorinated aliphatic hydrocarbons such as chlorobenzene, chloroethylene or methylene chloride; aliphatic hydrocarbons, such as cyclohexane or paraffines such as mineral oil fractions, as well as alcohols such as butanol or glycol and the ethers and esters thereof; ketones such as acetone, methyl ethyl ketone, methyl isobutyl ketone or cyclohexanone; strongly polar solvents such as dimethyl formamide, dimethyl sulfoxide and water. As liquefied gaseous carriers for example aerosol propellants such as halogenated hydrocarbons, butane, propane, nitrogen and carbon dioxide are included. As solid carriers for example natural fossil meals, e.g. kaoline, clay earth, talc, chalkstone, quartz, attapulgite, montmorillonite or diatomaceous earth, and synthetic fossil meals such as highly dispersed silicic acid, alumina and silicates are employed. As carriers for granulates for example broken and fractionated natural rocks, e.g. calcite, marble, pumice, sepiolite, dolomite, and granulates of inorganic and organic meals, as well as granulates prepared from organic materials such as sawdust, coconut shell, corn husk and tobacco stems can be used. As emulsifying agents and/or foaming agents non-ionic and anionic emulsifiers such as polyoxyethylene fatty acid ethers, polyoxyethylene fatty alcohol ethers, e.g. alkylarylpolyglycol ether, alkylsulfonates, alkylsulfates, arylsulfonates and protein hydrolysates, while as dispersing agents e.g. lignine, sulfite waste liquors and methyl cellulose may be employed.

The pesticidal compositions of the formula (VII) according to the invention may contain also adhesives such as carboxymethyl cellulose, natural and synthetic, powdery, granular or latex-like polymers, .e.g acacia gum, polyvinyl alcohol, polyvinyl acetate, etc.

The pesticidal compositions of the formula (VII) according to the invention may further contain various pigments such as inorganic pigments, e.g. iron oxide, titanium dioxide, ferrocyane blue and organic pigments, e.g. alizarine, azometal phthalocyanine pigments, as well as micronutrients, e.g. iron, manganese, boron, copper, cobalt, molybdenum and zinc salts.

The pesticidal compositions generally contain 0.1 to 95% by weight, preferably 0.5 to 90% by weight of active ingredient.

The active ingredients may be applied in the form of commercial formulations and/or ready-to-use formulations prepared therefrom.

The active ingredient concentration of the ready-to-use formulations prepared from the compositions may vary within wide limits, and generally is between 0.000 000 1 and 95% by weight, preferably 0.01 and 10% by weight.

The route of application always depends on the specific formulation used.

The invention further relates to a new process for the preparation of aminodiaryl sulfoxide derivatives of the formula (IX),

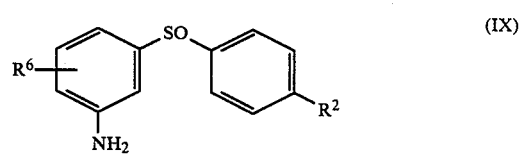

wherein
$R^6$ is halogen, alkoxy having from 1 to 6 carbon atoms or a group $-N(R^3, R^4)$, in which
$R^3$ and $R^4$ are hydrogen or alkyl having from 1 to 6 carbon atoms,
and acid addition salts thereof, by reducing either a nitrodiaryl sulfoxide of the formula (I) or (VII)

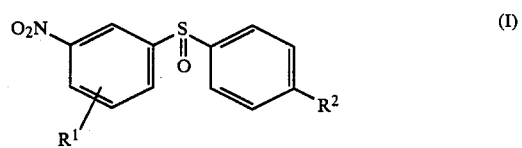

with a sulfide of the formula (X),

wherein
$M^1$ and $M^2$ are identical or different, and
$M^1$ is an alkali metal ion or ammonium ion,
$M^2$ is hydrogen, alkali metal ion or ammonium ion,
n is an integer between 1 and 9,
if desired, treating an aminodiaryl sulfoxide of the formula (IX) obtained with an acid.

In the formula (IX) $R^6$ and $R^2$ as halogen represent fluorine, chlorine, bromine or iodine, preferably chlorine; while as an alkoxy having from 1 to 6 carbon atoms they stand for a straight-chained or branched alkoxy having from 1 to 6 carbon atoms, such as methoxy, ethoxy, n-propoxy, isopropoxy, n-butoxy, sec.-butoxy, tert.-butoxy, isobutoxy, n-pentoxy, isopentoxy, n-hexyloxy, isohexyloxy, etc., preferably methoxy.

In the compounds of formula (X) $M^1$ and $M^2$ as an alkali metal ion for example represent a potassium or sodium ion.

Compounds of the formula (IX) are pharmaceutically active, and are particularly useful in the veterinary therapy as anthelmintics; on the other hand, show valuable pesticidal, particularly insecticidal, acaricidal and especially fungicidal and herbicidal activity.

The invention therefore relates to pharmaceutical compositions comprising as active ingredient at least one compound of formula (IX) or a physiologically acceptable salt thereof, in association with pharmaceutical carriers and/or excipients.

According to another aspect of the invention there are provided pesticidal compositions containing as active ingredient at least one compound of formula (IX) or a salt thereof, in association with at least one conventional carrier and optionally further additives.

The compounds of formula (IX) are further valuable intermediates in the preparation of other, new and known bioactive aromatic sulfoxide derivatives, such as benzimidazole- and other substituted diaminosulfoxide derivatives having anthelmintic and fungicidal activity (see e.g. the publishied German patent applications Nos. 2,406,584 and 2,739,215 and the U.S. Pat. No. 4,011,320). These compounds may for example be prepared by coupling the compounds according to the invention with a carbamic acid ester derivative.

The compounds of the formula (IX) where $R^6$ is a primary amino group para to the sulfinyl group and $R^2$ is defined above are valuable intermediates in the preparation of compounds of the formula (XI)

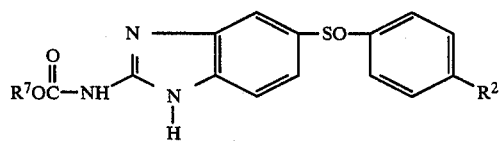

The compounds of the formula (XI) are prepared by reacting a compound of the formula (IX) where $R^6$ is a primary amino group para to the sulfinyl group with a compound of the formula (XII)

wherein
$R^7$ is $C_1$ to $C_6$ alkyl, $C_6$ to $C_{14}$ alkyl, preferably phenyl or naphthyl, or $C_7$ to $C_{20}$ aralkyl, preferably benzyl, and
$R^8$ is $C_1$ to $C_6$ alkyl, and the resulting mixture is refluxed for about 4 hours, preferably employing a halohydrocarbon solvent, followed by cooling to about 10° C. See Hungarian patent application 816/84.

Especially important starting materials are the new compounds of the formula (IX) where $R^6$ is a primary amino group in the para position relative to the sulfinyl group and $R^2$ is a phenyl or phenylthio group optionally substituted by at least one identical or different halogen or amino substituent.

The compounds of the formula (XI) are valuable anthelmintic compounds and are useful for the treatment of cattle, sheep, goats, pigs, fowl, and for the treatment of meat-eating animals such as dogs and cats. The compounds of the formula (XI) are especially effective for controlling parasites of the stomach and intestines as well as of the lungs.

The most wellknown compound of the formula (XI) is 5(6)-phenylsulfinyl-2-carbomethoxyamino-benzimidazole (oxfendazole) which is especially effective in the treatment of dichtyocaulosis in cattle, when administered in a dose of 4.5 mg/kg of body weight. The compounds of the formula (XI) are effective to the extent of 92 to 100% so that after treatment of the animals, practically no parasites remain. A further advantage to the compounds of the formula (XI) is their ability to control the parasites at every evelopment stage (i.e. ovule, larva, developed worm).

Specifically oxfendazole has been demonstrated to be effective against ostertagia in cattle at a dose of 4.5 mg/kg, and against monesia in sheep in a dose of 4.5 mg/kg and against chabertia and nematodirus battus in the very same dose. The effectiveness varies from 92 to 100%.

The compounds of the formula (IX), in which $R^6$ is a group $-N(R^3, R^4)$ being attached to the phenyl ring in para-position related to the sulfoxide group, and $R^3$ and $R^4$ both stand for hydrogen, $R^2$ stands for hydrogen or halogen or an alkyl or alkoxy group having from 1 to 6 carbon atoms, are known in the art, while the other compounds of formula (IX) are new. For the known compounds, however, no biological activity has been reported so far.

The known compound of the formula (IX), in which $R^2$ is hydrogen is e.g. disclosed in J. Med. Chem. 1975, (18), 1164. According to the prior art, this compound was for example prepared by reacting 5-chloro-2-nitroaniline with thiophenyl and oxidizing the phenyl-(3-amino-4-nitrophenyl) sulfide obtained with a peracid (see the above article) or, according to the published German patent appl. No. 1,438,120 by reacting 5-chloro-2-nitroaniline with sodium benzenesulfinate, and subsequently subjecting the phenyl-(3-amino-4-nitrophenyl) sulfoxide obtained by any of these procedures (in which the nitro group is in para-position related to the sulfoxide group, unlike in the instant compounds, in which the nitro group is in meta-position) to catalytic hydrogenation, in the presence of a palladium-on-charcoal catalyst. The drawbacks of these processes are as follows:

The known processes involve a catalytic hydrogenation step. During this step, due to the desactivating effect of the sulfur atom having a free electron pair, a large amount of noble metal catalyst is required. This results in substantial extra costs, even if the catalyst is regenerated and recycled most carefully. This, together with the expensive safety equipment to be used in catalytic hydrogenation processes, means that the synthesis cannot be carried out economically on industrial scale. A further disadvantge is that during catalytic hydrogenation, at a given temperature and pressure the sulfoxide compounds are reduced to sulfides and bis-nitrogen compounds are formed, and if in the formula (I) $R^1$ stands for halogen, also dehalogenation may take place during the catalytic hydrogenation of nitroaryl compounds as a side-reaction. Therefore, the product obtained must be further purified.

A nitro group can generally be reduced into an amino group also with a chemical reducing agent. A well-known chemical reducing agent is sodium dithionite, but if this compound is used for the desired reduction, sulfonation takes place as a side-reaction, which decreases the yield of the reaction and results in a contaminated product. Other reducing agents, e.g. SnCl$_2$ would make the reaction too expensive, while the reduction with iron powder in the presence of a ferro-salt and an acid is very difficult to carry out on industrial scale. The molecules which contain a nitro group in the para-position related to the sulfoxide group are very stable, therefore their nitrogen is rather resistant to chemical reducing agents, while under more agressive conditions other side-reactions affecting the bonds of the sulfur atom take also place, which result in a lower yield and a contaminated product. Among the reductions known in the art there is no one which would relate to the reduction of compounds of the formulae (I) or (VII) in which the nitro group is in meta-position related to the sulfoxide group.

We have surprisingly found that the reduction of a meta-nitrophenyl sulfoxide of the formulae (I) or (VII) can be carried out with an excellent yield, without side-reaction, and yields the desired product in high purity, if as a chemical reducing agent a compound of the formula (X) is used during the reduction. Typical representatives of the compounds of formula (X) are alkali metal sulfides, ammonium sulfide, alkali metal bisulfides, alkali metal polysulfides, etc. The yield and the purity of the product are better than in case of catalytic hydrogenation and the reaction conditions are very mild.

The process according to the invention is generally carried out in a (70:30)-(5:95) mixture of water and an aliphatic alcohol having from 1 to 6 carbon atoms, e.g. methanol, ethanol, n-propanol, isopropanol, n-butanol, sec.-butanol, tert.-butanol, etc. The reaction temperature and the reaction time depend on the starting materials employed. The reaction is preferably carried out between 60° C. and 100° C. in 0.5 to 6 hours.

The isolation of the product is carried out in a conventional manner, e.g. by diluting the reaction mixture with water, which results in the precipitation of the product in a pure form.

By the process according to the invention diaminodiaryl sulfoxides can be prepared with a better yield and in a better quality than by catalytic hydrogenation. In this manner the use of a large amount of noble metal catalyst (which is necessary in the catalytic hydrogenation due to the deactivating effect of sulfur) can be avoided, and the process can be carried out without any expensive safety apparatus. The reducing agents used in the process according to the invention are cheap, readily available commercial products. By this process more easily accessible starting materials can also be converted into the desired end products. The reduction is performed under mild conditions, i.e. under atmospheric pressure in a relatively short time. The process is practically free of corrosive side-effects and is easy to carry out even on industrial scale.

According to a still further aspect of the invention there are provided new compounds of the formula (IX)

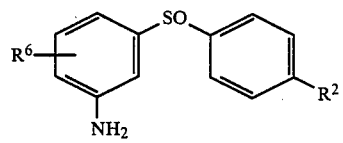

in which
R$^6$ is halogen, alkoxy having from 1 to 6 carbon atoms or a group —N(R$^3$, R$^4$), wherein
R$^3$ and R$^4$ are hydrogen or alkyl having from 1 to 6 carbon atoms,
R$^2$ is hydrogen, halogen, alkyl having from 1 to 6 carbon atoms, alkoxy having from 1 to 6 carbon atoms, or phenyl or phenylthio both optionally substituted by one or more, identical or different halogen(s) and/or nitro group(s),
provided that if R$^6$ stands for a group —N(R$^3$, R$^4$), in which R$^3$ and R$^4$ both are hydrogen, and R$^6$ is in para-position related to the sulfoxide group, then R$^2$ is other than hydrogen, halogen, alkyl having from 1 to 6 carbon atoms or alkoxy having from 1 to 6 carbon atoms, and acid addition salts thereof.

The compounds of formula (IX) can be converted into their acid addition salts by reaction with suitable acids. Suitable acids include e.g. inorganic acids, such as hydrogen halides, e.g. hydrochloric acid, hydrogen bromide, sulfuric acid, perhalogenic acids, e.g. perchloric acid, etc., organic acids, such as formic acid, acetic acid, propionic acid, glycolic acid, maleic acid, hydroxymaleic acid, fumaric acid, succinic acid, tartaric acid, ascorbic acid, citric acid, malic acid, salicylic acid, lactic acid, cinamic acid, benzoic acid, phenylacetic acid, p-aminobenzoic acid, p-hydroxybenzoic acid, p-aminosalycilic acid, etc., alkylsulfonic acids such as methanesulfonic acid, ethanesulfonic acid, etc., cycloaliphatic sulfonic acids, such as cyclohexylsulfonic acid; arylsulfonic acids, such as p-toluenesulfonic acid, naphthylsulfonic acid, sulfanilic acid, etc., amino acids, such as aspartic acid, glutamic acid, N-acetyl-aspartic acid, N-acetyl-glutamic acid, etc.

Salt formation can be carried out, for example, in an inert organic solvent, such as a C$_{1-6}$ aliphatic alcohol, by dissolving the compound of the formula (IX) in the solvent and adding the selected acid or a solution thereof formed with the same solvent to the first solution until it becomes slightly acidic (pH 5 to 6). Thereafter the acid addition salt separates and can be removed from the reaction mixture e.g. by filtration.

The compounds of the formula (IX) or the salts thereof, if desired, can be subjected to further purification e.g. recrystallization. The solvents used for recrystallization are selected depending on the solubility and crystallization properties of the compound to be crystallized.

The active compounds of the formula (IX) may be formulated for therapeutic purposes. The invention therefore relates also to pharmaceutical compositions comprising as active ingredient at least one compound of formula (IX) or a physiologically acceptable salt thereof, in association with pharmaceutical carriers and/or excipients. Carriers conventional for this purpose and suitable for parenteral or enteral administration as well as other additives may be used. As carriers solid or liquid compounds, for example water, gelatine, lactose, starch, pectin, magnesium stearate, stearic acid, talc, vegetable oils, such as peanut oil, olive oil, etc. can be used. The compounds can be formulated as conventional pharmaceutical formulations, for example in a solid (globular and angular pills, dragées, e.g. hard gelatine capsules) or liquid (injectable oily or aqueous solutions or suspensions) form. The quantity of the solid carrier can be varied within wide ranges, but preferably is between 25 mg. and 1 g. The compositions optionally contain also conventional pharmaceutical addivites, such as preserving agents, wetting agents, salts for adjusting the osmotic pressure, buffers, flavoring and aroma substances.

The compositions according to the invention optionally contain the compounds of the formula (IX) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

For use as pesticides, the compounds of the formula (IX(are formulated as conventional formulations, e.g. solutions, emulsions, soluble powders, suspensions, powder compositions, aerosol compositions, suspension and emulsion concentrates, powders for seed dressing. The compounds can be used for impregnating natural and synthetic materials, may be formulated as microcapsules, using polymeric substances and material suitable for coating seeds, or can be converted into formulations supplied with a burnable filling, such as smoke patrons, boxes, spirals, and warm or cold fog compositions, which may be applied by ULV (ultra-low-volume) technique.

The pesticidal compositions can be prepared in a manner known per se, for example by admixing the active ingredients with carriers, i.e. liquid solvents, liquefied gases under pressure and/or solid carriers. If desired, also surfactants, emulsifying and/or dispersing and/or foaming agents can be added to the system. If water is used as a carrier, as a co-solvent organic solvents may also be employed. The liquid solvents essentially include aromatic compounds such as xylene, toluene or alkylnaphthalenes; chlorinated aromatic or chlorinated aliphatic hydrocarbons such as chlorobenzene, chloroethylene or methylene chloride; aliphatic hydrocarbons such as cyclohexane or paraffines such as mineral oil fractions, as well as alcohols such as butanol or glycol and the ethers and esters thereof; ketones such as acetone, methyl ethyl ketone, methyl isobutyl ketone or cyclohexanone; strongly polar solvents such as dimethyl formamide, dimethyl sulfoxide and water. As liquefied gaseous carriers for example aerosol propellants such as halogenated hydrocarbons, butane, propane, nitrogen and carbon dioxide are meant. As solid carriers for example natural fossil meals, e.g. kaoline, clay earth, talc, chalkstone, quartz, attapulgite, montmorillonite or diatomaceous earth, and synthetic fossil meals such as higly dispersed silicic acid, alumina and silicates are employed. As carriers for granulates for example broken and fractionated natural rock, e.g. calcite, marble, pumice, sepiolite, dolomite, and granulates of inorganic and organic meals, as well as granulates prepared from organic materials such as sawdust, coconut shell, corn husk and tobacco stems can be used. As emulsifying agents and/or foaming agents non-ionic and anionic emulsifiers such as polyoxyethylene fatty acid ethers, polyoxyethylene fatty alcohol ethers, e.g. alkyl-arylpolyglycol ether, alkylsulfonates, alkylsulfates, arylsulfonates and protein hydrolysates, while as dispersing agents e.g. lignine, sulfite waste liquors and methy cellulose may be employed.

The pesticidal compositions containing the formula (IX) compound according to the invention may contain also adhesives such as carboxymethyl cellulose, natural and synthetic, powdery, granular or latex-like polymers, e.g. acacia gum, polyvinyl alcohol, polyvinyl acetate, etc.

The pesticidal compositions according to the invention may further contain various pigments such as inorganic pigments, e.g. iron oxide, titanium dioxide, ferrocyane blue and organic pigments, e.g. alizarine, azometal phthalocyanine pigments, as well as micronutrients, e.g. iron, manganese, boron, copper, cobalt, molybdenum and zinc salts.

The pesticidal compositions generally contain 0.1 to 95% by weight, preferably 0.5 to 90% by weight of active ingredient.

The active ingredients may be applied in the form of commercial formulations and/or ready-to-use formulations prepared therefrom.

The active ingredient concentration of the ready-to-use formulations prepared from the commercial pesticidal compositions may vary within wide limits, and generally is between 0.000 000 1 and 95% by weight, preferably 0.01 and 10% by weight.

The route of application always depends on the specific formulation used.

EXAMPLE 1

Sodium 4-chloro-3-nitro-benzenesulfinate

To a solution of 24 g. of sodium bicarbonate in 30 ml. of water 71.8 g. (0.57 moles) of solid, anhydrous sodium sulfite are added. To the homogenous solution a mixture of 58.4 g. (0.228 moles) of 4-chloro-3-nitro-benzenesulfonyl chloride and 24 g. of sodium bicarbonate is uniformly added in 2 hours, at 23° to 25° C. When the addition is complete, the suspension is stirred at 23° to 25° C. for 4 hours and subsequently, after addition of 200 ml. of toluene, at 35° C. for 15 minutes. It is then cooled to 23° to 25° C. and stirred. The product is filtered off and air dried.

56 g. of sodium 4-chloro-3-nitro-benzenesulfinate are obtained. According to the potassium permanganate analytical method the product contains 85% of active substance and 15% of water.

Yield: 90% of theoretical

EXAMPLE 2

4-Chloro-3-nitro-benzenesulfinic acid

The sodium salt prepared according to Example 1 is dissolved in 300 ml. of water at 40° C. and filtered at the same temperature. The filtrate is cooled to 10° to 15° C., acidified with 100 ml. of concentrated aqueous hydrochloric acid solution under thorough stirring, cooled to 5° C., filtered and the product obtained is dried at a temperature not exceeding 40° C.

43 g. of white, crystalline 4-chloro-3-nitro-benzenesulfinic acid are obtained.

Purity: 99%.

Melting point: 10° to 103° C.

Yield related to the sulfonyl chloride: 85% of theoretical.

EXAMPLE 3

Phenyl-(4-chloro-3-nitrophenyl) sulfoxide (a) 36 g. (0.1625 moles) of 4-chloro-3-nitro-benzenesulfinic acid prepared according to Example 2, 75 ml. of benzene and 15.1 ml. of thionyl chloride are admixed. The reaction mixture is boiled for one hour and distilled in vacuo at a temperature below 60° C. To the residue two further 25-ml-portions of benzene are added and the solvent is eliminated each time. To the residue weighing about 40 g. ($n_D^{24}=1.6240$), which is crude 4-chloro-3-nitro-benzenesulfinyl chloride, 20 ml. of dichloroethane are added, followed by the addition of 28.2 g. (0.21 moles) aluminium chloride under cooling, at a temperature below 40° C. Thereafter 35 ml. of benzene are added to the mixture at 40° C. within half an hour. The reaction mixture is stirred at 40° C. for two hours, diluted with 50 ml. of benzene, poured onto a mixture of 100 g. of ice and 50 ml. of water, the organic phase is extracted with 50 ml. of benzene. The combined benzene phases are decoloured with 5 g. of charcoal, filtered and the solvent is eliminated from the filtrate in vacuo.

45 g. of white phenyl-(4-chloro-3-nitro-phenyl) sulfoxide are obtained.

Melting point: 86° to 87° C.

Purity: 98% (according to high-pressure liquid chromatography).

Yield: 96% of theoretical.

(b) There are admixed 36 g. (0.1625 moles) of 4-chloro-3-nitro-benzenesulfinic acid prepared according to Example 2, 20 ml. of dichloroethane, 13.5 ml. (22 g., 0.185 moles) of thionyl chloride and 0.1 ml. of triethyl amine. The sulfinic acid is gradually dissolved while gas evolution is observed. The reaction mixture is heated at 50° C. for one hour, cooled to 5° to 10° C., and 28.2 g. (0.21 moles) of aluminium chloride are added to the solution, taking care that the temperature of the reaction mixture should not exceed 40° C. Thereafter 35 ml. of benzene are added to the mixture at 40° C., in half an hour. The reaction mixture is stirred at 40° C. for two hours, diluted with 50 ml. of benzene, and poured onto a mixture of 100 g. of ice and 50 ml. of water. The organic phase is separated, and the aqueous phase is extracted with 50 ml. of benzene. The combined benzene phases are decoloured with 5 g. of activated carbon, filtered and from the filtrate the overwhelming part of benzene is eliminated by distillation in vacuo, when a solid substance is precipitated. Thereafter, the remaining part of benzene is eliminated with methanol, under atmospheric pressure, so that the reaction mixture should contain about 60 to 70 ml. of methanol. The solution is then allowed to cool slowly. At 40° to 50° C. crystallization starts. When the product forms a thick crystal pulp, 100 ml. of water having a temperature of 40° to 50° C. are added to the reaction mixture at 40° to 50° C., initially at a low rate. The loose, finely dispersed suspension is cooled to 15° to 20° C. under vigorous stirring, filtered and dried.

45 g. of the desired compound are obtained. The physical properties of the product are identical with those of the product prepared according to variant (a).

EXAMPLE 4

Phenyl-(4-chloro-3-nitrophenyl) sulfoxide 23 g. (0.08 moles) of 84.7% sodium 4-chloro-3-nitrobenzenesulfinate prepared according to Example 1 are dissolved in 50 ml. of benzene. To the solution 9.2 ml. (0.112 moles) of phosphorus trichloride and 10 ml. of benzene are added at a temperature below 30° C., under vigorous stirring, in about 1.5 hours. The mixture is stirred for further 2.5 hours at 22° to 25° C., the benzene solution of the sulfinyl chloride derivative is decanted or filtered off by suction. From the solution obtained the solvent is eliminated in vacuo and distillation is repeated with two 20-ml portions of benzene. The pale-yellow oily sulfinyl chloride derivative ($n_D^{24}=1.6250$) is diluted with 18 ml. of benzene, and is then added to the suspension of 11.34 g. (0.085 moles) of aluminium chloride in 18 ml. of benzene at a temperature below 15° C. When the addition is complete, the reaction mixture is allowed to warm up to 40° C., and it is stirred at this temperature for two hours. The reaction mixture is then poured onto 100 ml. of icy water. The separated aqueous phase is extracted with 25 ml. of benzene. The combined benzene phases are decoloured with activated carbon, filtered and the filtrate is evaporated in vacuo.

21 g. of the desired compound are obtained.

Melting point: 86° to 87° C.

Yield: 95% of theoretical.

EXAMPLE 5

(4-Chloro-3-nitrophenyl)-4-methylphenyl sulfoxide

To about 40 g. of benzene- and thienyl chloride-free 4-chloro-3-nitrobenzene sulfinyl chloride prepared according to Example 3 100 ml. of toluene and subsequently 28.2 g. (0.21 moles) of aluminium chloride are added at 20° C., under cooling. The reaction mixture is stirred at 35° C. for 2.5 hours, and is further treated as described in Example 3.

42 g. of the desired compound are obtained.

Melting point: 82° to 84° C.

Yield: 87% of theoretical.

EXAMPLE 6

(4-Chloro-3-nitrophenyl)-4-chlorophenyl sulfoxide

The procedure described in Example 5 is followed, except that instead of toluene chlorobenzene is used, and the reaction mixture is stirred at 50° C. for 4 hours. The title compound is obtained with a yield of 89%.

Melting point: 110° to 112° C.

EXAMPLE 7

Phenyl-(4-methoxy-3-nitrophenyl) sulfoxide

4-Methoxy-3-nitrobenzene sulfonyl chloride (melting point: 66° C.) is reduced with sodium sulfite as described in Example 1, and the sodium 4-methoxy-3-nitrobenzene sulfinate is further treated as described in Example 4.

The title compound is obtained with a yield of 88%.

Melting point: 135° to 137° C.

EXAMPLE 8

2-Chloro-5-nitrobenzene sulfinic acid 321 ml. (4.7 moles) of chlorosulfonic acid and 79 g. (0.5 moles) of 4-chloro-nitrobenzene are stirred at 130° C. for 6 hours. The reaction mixture is then cooled to a temperature below 10° C. and is poured onto 750 ml. of icy water. The mixture is filtered at room temperature and the substance collected on the filter is washed acid-free with about 2 liters of water. The crude 2-chloro-5-nitrobenzene sulfonyl chloride obtained is subjected to the subsequent reaction steps without purification. 118 g. (0.935 moles) of anhydrous sodium sulfite and 20 g. of sodium bicarbonate are dissolved in 250 ml. of water, and to the solution obtained a mixture of the crude 2-chloro-5-nitrobenzene sulfonyl chloride and 20 g. of sodium bicarbonate is added at a temperature of 23° to 25° C., in one hour. The reaction mixture is stirred for two hours at a temperature of 23° to 25° C., and, after the addition of 200 ml. of toluene, for further 15 minutes. The mixture is stirred at 25° C. and the substance filtered off is washed with 100 ml. of toluene. The sodium 2-chloro-5-nitrobenzene sulfinate obtained is dissolved in 400 ml. of water at 40° C., and the solution is admixed with 200 ml. of toluene. The insoluble part is filtered off and the toluene phase is separated from the filtrate. The aqueous phase is cooled to 10° C., acidified with 100 ml. of concentrated aqueous hydrochloric acid solution and the precipitated crystals are stirred, filtered off at 10° C. and dried. 61 g. of 2-chloro-5-nitrobenzene sulfinic acid are obtained. Yield: 55% of theoretical related to 4-chloro-nitrobenzene.

Melting point: 128° to 130° C.

Purity: 98% (according to potassium permanganate analytical method).

EXAMPLE 9

Phenyl-(2-chloro-5-nitrophenyl) sulfoxide 26 g. (0.1625 moles) of 2-chloro-5-nitrobenzene sulfinic acid are admixed with 60 ml. of benzene and 36 ml. of thionyl chloride. The reaction mixture is boiled for one hour. Furtheron the procedure described in Example 3 is followed, except that instead of benzene dichloroethane is used for dilution and extraction.

40 g. of phenyl-(2-chloro-5-nitrophenyl) sulfoxide are obtained as a white microcrystalline substance.

Melting point: 150° to 152° C.

Purity: 97% (according to high-pressure liquid chromatography).

Yield: 85% of theoretical.

EXAMPLE 10

4-(4-Chloro-3-nitrobenzenesulfinyl)-biphenyl

The procedure described in Example 5 is followed except that instead of toluene biphenyl is employed. The desired compound is obtained with a yield of 90%.

Melting point: 98° to 99° C.

EXAMPLE 11

4-(4-Chloro-3-nitrophenylthio)-phenyl-(4-chloro-3-nitrophenyl) sulfoxide 36 g. (0.1625 moles) of 4-chloro-3-nitrobenzene sulfinic acid prepared according to Example 2, 35 ml. of benzene, 10.5 ml. (0.143 moles) of thionyl chloride and 0.1 g. of anhydrous ferric chloride are boiled for one hour. To the solution 28.2 g. (0.21 moles) of aluminium chloride are added at a temperature below 40° C. The reaction mixture is stirred at 40° C. for 2 hours, whereupon the procedure described in Example 3 is followed. The oily product obtained is dissolved in hot acetone, to the solution a small amount of aqueous methanol is added, whereupon the separated oil is dissolved in hot acetone and treated again with aqueous methanol. The oily portion is separated. Upon addition of acetone the desired compound is obtained in a crystalline form.

11.4 g. of the title compound are obtained.

Yield: 30% of theoretical.

Melting point: 144° to 146° C.

EXAMPLE 12

(4-Chloro-3-nitrophenyl)-4-methoxyphenyl sulfoxide

The reaction mixture containing 4-chloro-3-nitrobenzene sulfinyl chloride prepared as described in Example 3, variant (b) is released from thionyl chloride by distillation in vacuo. To the residue 50 ml. of dichloroethane and 21.6 g. of anisole are added, the mixture is cooled to −5° C. and 33.4 g. of aluminium chloride are portionwise added, taking care that the temperature of the mixture should not exceed 20° C. The reaction mixture is then kept at 20° C. for 4 hours, poured onto 300 ml. of icy water, extracted with dichloroethane and the solvent is eliminated from the organic solvent phase in vacuo.

46.5 g. of (4-chloro-3-nitrophenyl)-4-methoxyphenyl sulfoxide are obtained.

Yield: 92% of theoretical.

Melting point: 124° to 126° C.

EXAMPLE 13

(4-Chloro-3-nitrophenyl)-4-fluorophenyl sulfoxide

To about 40 g. of crude, benzene- and thionyl chloride-free 4-chloro-3-nitrobenzene sulfinyl chloride prepared according to any variant of Example 3 90 ml. of fluorobenzene are added, followed by the addition of 33.6 g. of aluminium chloride under cooling. The reaction mixture is then stirred at 55° C. for 5 hours and is further treated as described in Example 3, except that the reaction mixture is not diluted with benzene.

42 g. of the desired compound are obtained.

Yield: 86% of theoretical.

Melting point: 84° to 85° C.

EXAMPLE 14

(4-Bromophenyl)-(4-chloro-4-nitrophenyl) sulfoxide

To about 40 g. of crude 4-chloro-3-nitrobenzene sulfinyl chloride prepared according to any variant of Example 3 100 ml. of bromobenzene are added. Under cooling 33.6 g. of aluminium chloride are added to the mixture, which is then stirred at 50° C. for 3 hours and is further treated as described in Example 3, except that benzene is added to the reaction mixture after pouring onto water, and the excess of bromobenzene is eliminated from the reaction mixture by distillation at 60° to 70° C., under a pressure of 30 to 40 mmHg.

54.5 g. of the desired compound are obtained.

Yield: 93% of theoretical.

Melting point: 138° to 140° C.

EXAMPLE 15

4-Chlorophenyl-(2-chloro-5-nitrophenyl) sulfoxide 36 g. (0.1625 moles) of 2-chloro-5-nitrobenzene sulfinic acid prepared according to Example 8 are converted into 2-chloro-5-nitrobenzene sulfinyl chloride as described in Example 3. It is then released from benzene and thionyl chloride, diluted with 100 ml. of chlorobenzene, and to the mixture 28.2 g. of aluminium chloride are added under stirring. The reaction mixture is then stirred at 55° C. for 5 hours and is further treated as described in Example 3, except that the dilution with benzene is carried out only after pouring onto water.

44 g. of the desired compound are obtained.

Yield: 86% of theoretical.

Melting point: 142° to 144° C.

EXAMPLE 16

(4-Ethoxy-3-nitrophenyl)-phenyl sulfoxide

The procedure described in Example 7 is followed, except that 4-ethoxy-3-nitrobenzene sulfonyl chloride is used as a starting material and from this sodium 4-ethoxy-3-nitrobenzene sulfinate is prepared as described in Example 1, with a yield of 70% which is then treated further as described in Example 4.

The desired compound is obtained with a yield of 86%.

Melting point: 119° to 121° C.

EXAMPLE 17

1-(4-Bromophenyl)-4-(4-chloro-3-nitrophenylsulfinyl)-benzene

The procedure described in Example 5 is followed, except that instead of toluene 4-bromo-biphenyl is used. The desired compound is obtained with a yield of 80%.

Melting point: 173° to 175° C.

EXAMPLE 18

(4-Chloro-3-nitrophenyl)-4-methylthiophenyl sulfoxide

The procedure described in Example 5 is followed, except that instead of toluene thioanisole is used.

EXAMPLE 19

1-(4-Nitrophenyl) 4-(4-chloro-3-nitrophenylsulfinyl) benzene

The procedure described in Example 5 is followed, except that toluene is replaced by 4-nitro-biphenyl. The title compound is obtained with a yield of 50%. Melting point: 220° to 222° C.

EXAMPLE 20

Phenyl-(4-amino-3-nitrophenyl) sulfoxide 28.15 g. (0.1 mole) of phenyl-(4-chloro-3-nitrophenyl) sulfoxide are admixed with 76.5 ml. (0.9 moles) of an aqueous ammonium hydroxide solution having a concentration of 20 g./100 ml. and 93.5 ml. of isopropanol. The reaction mixture is heated up to 100° C. and the conversion grade of amination is controlled by gas chromatography or high pressure liquid chromatography. After about 10 hours only about 2% of the starting material are present in the reaction mixture. This time the reaction mixture is slowly cooled to 30° to 40° C., whereupon 15 ml. of water are added under stirring, the mixture is stirred at room temperature for half an hour, filtered, the solid remaining on the filter is washed with water and dried.

25.3 g. of phenyl-(4-amino-3-nitrophenyl) sulfoxide are obtained as a yellow crystalline material.

Purity: 98% (determined by high pressure liquid chromatography).

Melting point: 146° to 147° C.

Yield: 95% of theoretical.

EXAMPLE 21

Phenyl-(4-amino-3-nitrophenyl) sulfoxide 27.7 g. (0.1 moles) of phenyl-(4-methoxy-3-nitrophenyl) sulfoxide are admixed with 76.5 ml. (0.9 moles) of an aqueous ammonium hydroxide solution having a concentration of 20 g./100 ml. and 93.5 ml. of isopropanol. The reaction mixture is kept at 100° C. for 16 hours.

As a result, the concentration of the starting material in the reaction mixture decreases below 2%.

The reaction mixture is further treated as described in Example 20 25 g. of the aimed compound are obtained.

Purity: 98%.

Melting point: 146° to 147° C.

Yield: 93.5% of theoretical.

EXAMPLE 22

Phenyl-(4-amino-3-nitrophenyl) sulfoxide

A mixture of 28.15 g. (0.1 mole) of phenyl-(4-chloro-3-nitrophenyl) sulfoxide, 45 g. 1.0 mole of formic acid amide, 94 ml. of isopropanol and 50 ml. of water is heated at 150° C. for 15 hours. The reaction mixture is further treated as described in Example 20.

22 g. of the desired compound are obtained.

Yield: 81% of theoretical.

Melting point: 146° to 147° C.

EXAMPLE 23

Phenyl-(4-amino-3-nitrophenyl) sulfoxide

To a mixture of 80 ml. of ethylene glycol, 4 ml. of water and 28.15 g. (0.1 mole) of phenyl-(4-chloro-3-nitrophenyl) sulfoxide 60 g. (1.0 mole) of urea are added at 170° C., in about 2 hours, and the reaction mixture is stirred at this temperature for two hours. The progress of the reaction is monitored by thin layer chromatography (5:1 mixture of benzene and methanol, Alufolie Kieselgel 60 $F_{254}$, detecting by u.v. light). When the conversion is not complete, further 18 g. (0.3 moles) of urea are added to the reaction mixture portionswise, and the mixture is stirred at 170° C. for an additional hour. After the addition of 70 ml. of water the reaction mixture is treated as described in Example 20.

21 g. of phenyl-(4-amino-3-nitrophenyl) sulfoxide are obtained.

Yield: 77% of theoretical.

Melting point: 146° to 147° C.

EXAMPLE 24

Phenyl-(4-dimethylamino-3-nitrophenyl) sulfoxide

A mixture of 28.15 g. (0.1 mole) of phenyl-(4-chloro-3-nitrophenyl) sulfoxide, 150 g. (1.0 mole) of a 30% aqueous dimethyl amine solution and 150 ml. of isopropanol is heated at 120° C. for 6 hours, whereupon the reaction mixture is diluted with 100 ml. of water, and furtheron the procedure described in Example 20 is followed.

25.5 g. of phenyl-(4-dimethylamino-3-nitrophenyl) sulfoxide are obtained as a yellow crystalline substance.

Purity: 98%.

Melting point: 125° to 126° C.

Yield: 86% of theoretical.

EXAMPLE 25

Phenyl-(4-dimethylamino-3-nitrophenyl) sulfoxide

The procedure described in Example 24 is followed except that dimethyl amine is replaced by 73 g. (1.0 mole) of dimethyl formamide and 75 ml. of water. The reaction is carried out at 120° C. for 15 hours.

24 g. of the desired compound are obtained.

Yield: 81% of theoretical.

Melting point: 124° to 126° C.

EXAMPLE 26

(4-Amino-3-nitrophenyl)-4-methylphenyl sulfoxide

The procedure described in Example 20 is followed, except that as a starting material instead of phenyl-(4-chloro-3-nitrophenyl) sulfoxide a corresponding amount of (4-chloro-3-nitrophenyl)-4-methylphenyl sulfoxide is used.
Yield: 80%.
Melting point: 161° to 163° C.

EXAMPLE 27

(4-Amino-3-nitrophenyl)-4-chlorophenyl sulfoxide

The procedure described in Example 20 is followed, except that as a starting material instead of phenyl-(4-chloro-3-nitrophenyl) sulfoxide a corresponding amount of (4-chloro-3-nitrophenyl)-4-chlorophenyl sulfoxide is employed.
Yield: 77%.
Melting point: 176° to 179° C.

EXAMPLE 28

Phenyl-(2-amino-5-nitrophenyl) sulfoxide

The procedure described in Example 20 is followed, except that as a starting material instead of phenyl-(4-chloro-3-nitrophenyl) sulfoxide a corresponding amount of phenyl-(2-chloro-5-nitrophenyl) sulfoxide is employed, and the reaction is carried out at 140° C. for 20 hours.
Yield: 84%.
Melting point: 188° to 191° C.

EXAMPLE 29

4-(4-Amino-3-nitrophenyl-sulfinyl)-biphenyl

The procedure described in Example 20 is followed, except that as a starting material instead of phenyl-(4-chloro-3-nitrophenyl) sulfoxide a corresponding amount of 4-(4-chloro-3-nitrophenyl-sulfinyl)-biphenyl is employed.
Yield: 81%.
Melting point: 198° to 200° C.

EXAMPLE 30

[4-(4-Chloro-3-nitrophenylthio)-phenyl]-(4-amino-3-nitrophenyl) sulfoxide

The procedure described in Example 20 is followed, except that as a starting material instead of phenyl-(4-chloro-3-nitrophenyl) sulfoxide a corresponding amount of [4-(4-chloro-3-nitrophenylthio)-phenyl]-(4-chloro-3-nitrophenyl) sulfoxide is employed, and the amination is carried out at 110° C. for 20 hours. The product obtained is a mixture of two substances, which can be separated by chromatography.

The title compound is obtained with a yield of 65%; melting point: 170° to 172° C.

In addition [4-(4-amino-3-nitrophenylthio)-phenyl]-(4-amino-3-nitrophenyl) sulfoxide, melting at 200° to 202° C. is obtained, with a yield of 16%.

EXAMPLE 31

(4-Amino-3-nitrophenyl)-4-methoxyphenyl sulfoxide

The procedure described in Example 20 is followed except that as a starting material instead of phenyl-(4-chloro-3-nitrophenyl) sulfoxide a corresponding amount of (4-chloro-3-nitrophenyl)-4-methoxyphenyl sulfoxide is used.
Yield: 83%.
Melting point: 197° to 199° C.

EXAMPLE 32

(4-Amino-3-nitrophenyl)-4-fluorophenyl sulfoxide

The procedure described in Example 20 is followed, except that as a starting material instead of phenyl-(4-chloro-3-nitrophenyl) sulfoxide a corresponding amount of 4-fluorophenyl-(4-chloro-3-nitrophenyl) sulfoxide is employed.
Melting point: 169° to 171° C.
Yield: 85%.

EXAMPLE 33

(4-Amino-3-nitrophenyl 4-bromophenyl sulfoxide

The procedure described in Example 20 is followed, except that as a starting material instead of phenyl-(4-chloro-3-nitrophenyl)sulfoxide a corresponding amount of 4-bromophenyl-(4-chloro-3-nitrophenyl)sulfoxide is employed.
Melting point: 202° to 205° C.
Yield: 87%

EXAMPLE 34

(4-Ethylamino-3-nitrophenyl)-phenyl sulfoxide

A mixture of 28.15 g. (0.1 mole) of phenyl-(4-chloro-3-nitrophenyl)sulfoxide, 50 g. (0.515 moles) of a 46.4% methanolic ethylamine solution, 70 ml. of water and 50 ml. of ethanol is heated at 100° C. for 5.5 hours. The reaction mixture is then cooled to room temperature under stirring, stirred at room temperature for half an hour, filtered and the substance remaining on the filter is washed with water and dried.

25 g. of the desired compound are obtained as a yellow crystalline substance.
Yield: 86% of theoretical.
Melting point: 122° to 124° C.

EXAMPLE 35

(4-sec.-Butylamino-3-nitrophenyl)-phenyl sulfoxide

A mixture of 28.15 g. (0.1 mole) of phenyl-(4-chloro-3-nitrophenyl)sulfoxide, 58.4 g. (0.8 moles) of sec.-butylamine, 90 ml. of isopropanol and 50 ml. of water is heated at 100° C. for 6 hours. The reaction mixture is further treated as described in Example 34.

28 g. of the desired compound are obtained.
Yield: 88% of theoretical.
Melting point: 88° to 91° C.

EXAMPLE 36

(2-Amino-5-nitrophenyl)-4-chlorophenyl sulfoxide

The procedure described in Example 20 is followed, except that as a starting material instead of phenyl-(4-chloro-3-nitrophenyl)sulfoxide a corresponding amount of (2-chloro-5-nitrophenyl)-4-chlorophenyl sulfoxide is used and the reaction is performed at 140° C. for 2 hours.

EXAMPLE 37

1-(4-bromophenyl)-4-(4-amino-3-nitrophenyl-sulfinyl)-benzene

The procedure described in Example 20 is followed, except that as a starting material instead of phenyl-(4- chloro-3-nitrophenyl)sulfoxide a corresponding amount of 1-(4-bromophenyl)-4-(4-chloro-3-nitrophenylsulfinyl)benzene is used.

The desired compound is obtained with a yield of 82%.

Melting point: 218° to 220° C.

EXAMPLE 38

(4-Amino-3-nitrophenyl)-(4-methylthiophenyl)sulfoxide

The procedure described in Example 20 is followed, except that as starting material instead of phenyl-(4-chloro-3-nitrophenyl)sulfoxide a corresponding amount of (4-chloro-3-nitrophenyl)-4-methylthiophenyl sulfoxide is employed.

EXAMPLE 39

Phenyl-(3,4-diaminophenyl) sulfoxide

To a suspension of 20 g. (0.076 moles) of phenyl-(4-amino-3-nitrophenyl) sulfoxide in 80 ml. of methanol a solution of 22 g. (0.17 moles) of sodium sulfide of 60% purity in 25 ml of water is added in one hour under boiling. The reaction mixture is then refluxed for 3 hours.

The progress of the reaction is monitored by thin layer chromatography (5:1 mixture of benzene and methanol, Merck Kieselgel/60F$_{254}$ Alufoil, u.v. detection). Thereafter 1 g. of celite or 1 g. of activated carbon is added to the reaction mixture, which is then filtered while hot. The filtrate is slowly cooled to room temperature, under stirring. The precipitated substance is filtered off. The material remaining on the filter is washed base-free with water and dried at 50° to 60° C.

16 g. of greyish-beige phenyl-(3,4-diaminophenyl)sulfoxide are obtained, melting at 149° to 150° C.

From the mother liquor about 20 ml. of solvent are distilled off in vacuo, the distillation residue is diluted with 30 ml. of water and the precipitate is filtered off. The product weighing 1.2 g. is recrystallized from 6 ml. of 60% methanol to yield a further 1 g. of the desired compound, which has the same melting point as the compound prepared in the previous step.

Total yield: 95% of theoretical.

EXAMPLE 40

3,4-Diaminophenyl-4-methylphenyl sulfoxide

To a suspension of 21.2 g. (0.076 moles) of (4-amino-3-nitrophenyl)-4-methylphenyl sulfoxide in 80 ml. of methanol a solution of 22 g. (0.17 moles) of sodium sulfide of 60% purity in 25 ml. of water is added in one hour, under boiling. The reaction mixture is refluxed for 3 hours, and the progress of the reaction is monitored by thin layer chromatography. Thereafter 1 g. of celite is added to the reaction mixture, which is then filtered while hot. The filtrate is diluted with 50 ml. of water, and is slowly cooled to room temperature. The precipitate is filtered off, and the substance remaining on the filter is washed base-free with water. The product is then dried at 50° to 60° C. to yield 17 g. of the title compound, melting at 131° to 132° C.

Yield: 91% of theoretical.

EXAMPLE 41

Phenyl-(3-amino-4-dimethylaminophenyl) sulfoxide

Following the procedure described in Example 39 but using as a starting material instead of (4-amino-3-nitrophenyl)-4-methylphenyl sulfoxide a corresponding amount of phenyl-(4-dimethylamino-3-nitrophenyl) sulfoxide, the title compound is obtained.

Melting point: 85° to 86° C.

Yield: 90% of theoretical.

EXAMPLE 42

(3,4-Diaminophenyl)-(4-chlorophenyl) sulfoxide

Following the procedure described in Example 40 but using as a starting material instead of (4-amino-3-nitrophenyl)-4-methylphenyl sulfoxide a corresponding amount of (4-amino-3-nitrophenyl)-4-chlorophenyl sulfoxide, the title compound is obtained.

Melting point: 152° to 153° C.

Yield: 92% of theoretical.

EXAMPLE 43

4-(3,4-Diaminophenylsulfinyl)-biphenyl

Following the procedure described in Example 40 but using as a starting material instead of (4-amino-3-nitrophenyl)-4-methylphenyl sulfoxide a corresponding amount of 4-(4-amino-3-nitrophenylsulfinyl)-biphenyl, the title compound is obtained.

Melting point: 199° to 201° C.

Yield: 95% of theoretical.

EXAMPLE 44

[4-(4-Chloro-3-aminophenylthio)-phenyl]-3,4-diaminophenyl sulfoxide

Following the procedure described in Example 40 but using as a starting material instead of (4-amino-3-nitrophenyl)-4-methylphenyl sulfoxide a corresponding amount of [4-(4-chloro-3-nitrophenylthio)-phenyl]-4-amino-3-nitrophenyl sulfoxide, the title compound is obtained.

EXAMPLE 45

Phenyl-(3-amino-4-chlorophenyl) sulfoxide

Following the procedure described in Example 40 but using as a starting material instead of (4-amino-3-nitrophenyl)-4-methylphenyl sulfoxide a corresponding amount of phenyl-(4-chloro-3-nitrophenyl) sulfoxide, the title compound is obtained.

Melting point: 89° to 90° C.

Yield: 90% of theoretical.

EXAMPLE 46

3,4-Diaminophenyl-4-methoxyphenyl sulfoxide

Following the procedure described in Example 40 but using as a starting material instead of (4-amino-3-nitrophenyl)-4-methylphenyl sulfoxide a corresponding amount of (4-amino-3-nitrophenyl)-4-methoxyphenyl sulfoxide, the title compound is obtained.

Melting point: 145° to 147° C.

Yield: 90%.

EXAMPLE 47

3,4-Diaminophenyl-4-fluorophenyl sulfoxide

Following the procedure described in Example 40 but using as a starting material instead of (4-amino-3-nitrophenyl)-4-methylphenyl sulfoxide a corresponding amount of (4-amino-3-nitrophenyl)-4-fluorophenyl sulfoxide, the title compound is obtained.

Melting point: 81° to 83° C.

Yield: 91%.

EXAMPLE 48

4-Bromophenyl-3,4-diaminophenyl sulfoxide

Following the procedure described in Example 40 but using as a starting material instead of (4-amino-3-nitrophenyl)-4-methylphenyl sulfoxide a corresponding amount of 4-bromophenyl-(4-amino-3-nitrophenyl) sulfoxide, the title compound is obtained.

EXAMPLE 49

(3-Amino-4-methoxyphenyl)-phenyl sulfoxide

Following the procedure described in Example 40 but using as a starting material instead of (4-amino-3-nitrophenyl)-4-methylphenyl sulfoxide a corresponding amount of (4-methoxy-3-nitrophenyl)-phenyl sulfoxide, the title compound is obtained.
Melting point: 113° to 115° C.
Yield: 89% of theoretical.

EXAMPLE 50

(3-Amino-4-ethylaminophenyl)-phenyl sulfoxide

Following the procedure described in Example 40 but using as a starting material instead of (4-amino-3-nitrophenyl)-4-methylphenyl sulfoxide a corresponding amount of (4-ethylamino-3-nitrophenyl)-phenyl sulfoxide, the title compound is obtained.
Melting point: 140° to 142° C.
Yield: 93% of theoretical.

EXAMPLE 51

1-(4-Bromophenyl)-4-(3,4-diaminophenylsulfinyl)-benzene

Following the procedure described in Example 40 but using as a starting material instead of (4-amino-3-nitrophenyl)-4-methylphenyl sulfoxide a corresponding amount of 1-(4-bromophenyl)-4-(4-amino-3-nitrophenylsulfinyl)-benzene, the title compound is obtained; M.P.=161°–164° C.

EXAMPLE 52

3,4-Diaminophenyl-4-methylthiophenyl sulfoxide

Following the procedure described in Example 40 but using as a starting material instead of (4-amino-3-nitrophenyl)-4-methylphenyl sulfoxide a corresponding amount of (4-amino-3-nitrophenyl)-4-methylthiophenyl sulfoxide, the title compound is obtained.

EXAMPLE 53

(3-Amino-4-chlorophenyl)-4-fluorophenyl sulfoxide

Following the procedure described in Example 40 but using as a starting material instead of (4-amino-3-nitrophenyl)-4-methylphenyl sulfoxide a corresponding amount of 4-fluorophenyl-(4-chloro-3-nitrophenyl) sulfoxide, the title compound is obtained.
Yield: 90%; M.P.=82°–85° C.

EXAMPLE 54

(3-Amino-4-chlorophenyl)-4-methylphenyl sulfoxide

Following the procedure described in Example 40 but using as a starting material instead of (4-amino-3-nitrophenyl)-4-methylphenyl sulfoxide a corresponding amount of (4-chloro-3-nitrophenyl)-4-methylphenyl sulfoxide, the title compound is obtained; M.P.=119°–121° C.
Yield: 88%; M.R. 119°–121° C.

EXAMPLE 55

(3-Amino-4-chlorophenyl)-4-bromphenyl sulfoxide

Following the procedure described in Example 40 but using as a starting material instead of (4-amino-3-nitrophenyl)-4-methylphenyl sulfoxide a corresponding amount of 4-bromophenyl-4-(4-chloro-3-nitrophenyl) sulfoxide, the title compound is obtained.
Yield: 87%; M.P.=119°–122° C.

EXAMPLE 56

(5-Amino-2-chlorophenyl)-phenyl sulfoxide

Following the procedure described in Example 40 but using as a starting material instead of (4-amino-3-nitrophenyl)-4-methylphenyl sulfoxide a corresponding amount of (2-chloro-5-nitrophenyl)-phenyl sulfoxide, the title compound is obtained.
Yield: 89%; M.P.=152°–155° C.

EXAMPLE 57

(5-Amino-2-chlorophenyl)-4-chlorophenyl sulfoxide

Following the procedure described in Example 40 but using as a starting material instead of (4-amino-3-nitrophenyl)-4-methylphenyl sulfoxide a corresponding amount of 4-chlorophenyl-(2-chloro-5-nitrophenyl) sulfoxide, the title compound is obtained.
Yield: 87%; M.P.=156°–159° C.

EXAMPLE 58

(3-Amino-4-chlorophenyl)-4-methoxyphenyl sulfoxide

Following the procedure described in Example 40 but using as a starting material instead of (4-amino-3-nitrophenyl)-4-methylphenyl sulfoxide a corresponding amount of (4-chloro-3-nitrophenyl)-4-methoxyphenyl sulfoxide, the title compound is obtained.
Yield: 86%; M.P.=103°–105° C.

EXAMPLE 59

4-(3-Amino-4-chlorophenylsulfinyl)-biphenyl

Following the procedure described in Example 40 but using as a starting material instead of (4-amino-3-nitrophenyl)-4-methylphenyl sulfoxide a corresponding amount of 4-(4-chloro-3-nitrophenylsulfinyl)-biphenyl, the title compound is obtained.
Yield: 85%; M.P.=134°–137° C.

EXAMPLE 60

1-(4-Bromophenyl)-4-(3-amino-4-chlorophenylsulfinyl)-benzene

Following the procedure described in Example 40 but using as a starting material instead of (4-amino-3-nitrophenyl)-4-methylphenyl sulfoxide a corresponding amount of 1-(4-bromophenyl)-4-(4-chloro-3-nitrophenylsulfinyl)benzene, the title compound is obtained.
Yield: 88%.

EXAMPLE 61

A mixture of 23.2 g (0.1 moles) of phenyl-(3,4-diaminophenyl)-sulfoxide, 20 g (0.15 moles) of 4-methoxycarbonyl-0-methylisourea, 100 ml of dichloroethane and 15 ml of acetic acid is refluxed for 4 hours. The reaction mixture is then cooled to 10° C. The precipitated material is separated by filtration, washed three times with 50 ml of methanol on the filter, and finally dried at 70° to 80° C. 28.4 g (90%) of the desired 5(6)-phenylsulfinyl-2-carbomethoxyamino-benzimidazole are obtained (mp 254° C., decomposition).

EXAMPLE 62

5(6)-(4-Biphenyl sulfinyl)-2-carbomethoxyamino-benzimidazole

We proceed as in Example 61 with the only difference that we use as a starting material an appropriate quantity of 4-(3,4-diamino-phenylsulfinyl-biphenyl instead of phenyl-)3,4-diaminophenyl-sulfoxide.

The melting point of the chemical as per the title is 287° C. (decomposition)

Yield: 92%.

EXAMPLE 63

5(6)-(4-methyl-phenylsulfinyl)-2-carbomethoxyamino-benzimidazole

We proceed in every respect in accordance with the procedure described in Example 61 with the only difference that we use as starting material an appropriate quantity of (4-methylphenyl)-(3,4-diamino-phenyl)-sulfoxide instead of phenyl-(3,4-diamino-phenyl)-sulfoxide.

The boiling point of the chemical of the title is 267° C. (it decomposes).

EXAMPLE 64

5(6)-(4-chloro-phenylsulfinyl)-2-carbomethoxyamino-benzimidazole

We proceed as outlined in Example 61 with the difference that we use as starting material an appropriate quantity of (4-chloro-phenyl)-3(3,4-diamino-phenyl)-sulfoxide instead of phenyl-(3,4-diamino-phenyl)-sulfoxide.

The melting point of the chemical of the title is 292° C. (decomposition).

EXAMPLE 65

5(6)-(4-methoxy-phenylsulfinyl)-2-carbomethoxyamino-benzimidazol

We follow the procedure described in Example 61 with the difference that we use as starting material an appropriate quantity of (4-methoxy-phenyl)-(3,4-diamino-phenyl)-sulfoxide instead of phenyl-(3,4-diamino-phenyl)-sulfoxide.

The melting point of the chemical of the title is 275° C. (decomposition).

EXAMPLE 66

5(6)-(4-fluoro-phenylsulfinyl)-2-carbomethoxyamino-benzimidazole

We proceed in accordance with the procedure described in Example 61 with the difference that we use as starting material an appropriate quantity of (4-fluorophenyl)-(3,4-diamino-phenyl)sulfoxide in lieu of phenyl-(3,4-diamino-phenyl)-sulfoxide.

The melting point of the product of the title is 273° C. (decomposition).

We claim:

1. Process for the preparation of nitrodiaryl sulfoxides of the formula (I),

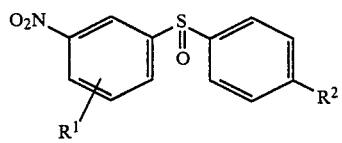

wherein
$R^1$ is halogen or alkoxy having from 1 to 6 carbon atoms,
$R^2$ is hydrogen, halogen, alkyl having from 1 to 6 carbon atoms, alkoxy having from 1 to 6 carbon atoms, or phenyl or phenylthio unsubstituted or substituted by one to five identical or different halogen or nitro groups,
which comprises reducing an arylsulfonyl halide of the formula (II),

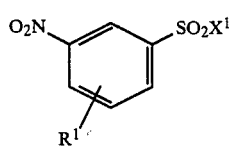

wherein
$X^1$ is halogen,
with an alkali metal sulfite, treating the arylsulfinate of the formula (III)

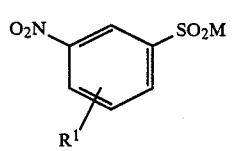

obtained, in which
M is an alkali metal,
with an acid, reacting the arylsulfinic acid of the formula (IV)

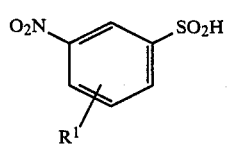

obtained, or the arylsulfinate of the formula (III), with a halogenating agent, and reacting the resulting arylsulfinyl halide of the formula (V)

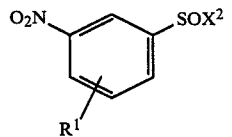

obtained, in which
$X^2$ is halogen,
with a benzene derivative of the formula (VI),

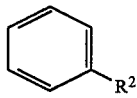 (VI)

2. Process as claimed in claim 1, in which during the reduction 1.1 to 4 moles of an alkali metal sulfite are used per mole of arylsulfonyl halide of the formula (II).

3. Process as claimed in claim 1, in which the reduction of an arylsulfonyl halide of formula (II), is carried out between 20° C. and 50° C.

4. Process as claimed in claim 1, in which the reduction of an arylsulfonyl halide of formula (II), is carried out in a slightly alkaline medium.

5. Process as claimed in claim 1, in which the arylsulfinate of the formula (III), is treated with an excess of a strong mineral acid.

6. A process as claimed in claim 1, in which the arylsulfinyl halide of the formula (V), is reacted with the benzene derivative of the formula (VI), after elimination of the excess of halogenating agent, without isolation of said formula (V) compound.

7. A process as claimed in claim 1, in which in the reaction of an arylsulfinyl halide of formula (V), with a benzene derivative of the formula (VI), wherein as a Lewis acid 1.1 to 1.8 moles of aluminium chloride are employed per mole of arylsulfinyl chloride.

8. Process as claimed in claim 1, in which the reaction of an arylsulfinyl halide of the formula (V), with a benzene derivative of the formula (VI), is carried out at a temperature between 0° C. and 80° C.

* * * * *